(12) United States Patent
Siani-Rose et al.

(10) Patent No.: US 7,133,780 B2
(45) Date of Patent: Nov. 7, 2006

(54) COMPUTER SOFTWARE FOR AUTOMATED ANNOTATION OF BIOLOGICAL SEQUENCES

(75) Inventors: Michael A Siani-Rose, San Francisco, CA (US); Ron Shigeta, Berkeley, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/683,264

(22) Filed: Dec. 5, 2001

(65) Prior Publication Data

US 2003/0023384 A1 Jan. 30, 2003

Related U.S. Application Data

(60) Provisional application No. 60/285,403, filed on Apr. 20, 2001, provisional application No. 60/285,144, filed on Apr. 19, 2001.

(51) Int. Cl.
*G06F 19/00* (2006.01)
(52) U.S. Cl. .......................................... 702/20; 702/19
(58) Field of Classification Search ................... 702/19, 702/20
See application file for complete search history.

(56) References Cited

U.S. PATENT DOCUMENTS 6,377,893 B1 * 4/2002 Benner ......................... 702/20

OTHER PUBLICATIONS

Eddy, S. R. Profile hidden Markov models. Bioinformatics. 1998, vol. 14, No. 9, pp. 755-763.*
Berman et al., "The Protein Data Bank," *Nuc. Acids Res.*, 28(1):235-242 (2000).
Brenner et al., "The ASTRAL compendium for protein structure and sequence analysis," *Nuc. Acids Res.*, 28(1):254-256 (2000).
Karplus et al., "Hidden Markov models for detecting remote protein homologies," *Bioinformatics*, 14(10):846-856 (1998).
Haughey et al., *SAM Sequence Alignment and Modeling Software System*, Baskin Center for Computer Engineering and Science, University of California, Technical Report UCSC-CRL-99-11, pp. 1-154 (2001).
Altschul et al., "Gapped BLAST and PSI-BLAST: a new generation of protein database search programs," *Nuc. Acids Res.*, 25(17):3389-3402 (1997).
Apweiler et al., "The InterPro database, an integrated documentation resource for protein families, domains and functional sites," *Nuc. Acids Res.*, 29(1):37-40 (2001).
Aravind et al., "Gleaning Non-trivial Structural, Functional and Evolutionary Information About Proteins by Iterative Database Searches," *J. Mol. Biol.*, 287:1023-1040 (1999).
Barker et al., "Protein Information Resource: a community resource for expert annotation of protein data," *Nuc. Acids Res.*, 29(1):29-32 (2001).
Barrett et al., "Scoring hidden Markov models," *CABIOS*, 13(2):191-199 (1997).
Bateman et al., "The Pfam Protein Families Database," *Nuc: Acids Res.*, 28(1):263-266 (2000).
Birney et al., "Using *Genewise* in the *Drosophila* Annotation Experiment," *Genome Research*, 10:547-548 (2000).
Murzin et al., "SCOP: A Structural Classification of Proteins Database for the Investigation of Sequences and Structures," *J. Mol. Biol.*, 247:536-540 (1995).
Geetha et al., "Comparing protein sequence-based and predicted secondary structure-based methods for identification of remote homologs," *Protein Engineering*, 12(7):527-534 (1999).
Grundy et al., "Meta-MEME: motif-based hidden Markov models of protein families," *CABIOS*, 13(4):397-406 (1997).
Hargbo et al., "Hidden Markov Models That Use Predicted Secondary Structures For Fold Recognition," *Proteins: Structure, Function, and Genetics*, 36:68-76 (1999).
Park et al., "Sequence Comparisons Using Multiple Sequences Detect Three times as Many Remote Homologues as Pairwise Methods," *J. Mol. Biol.*, 284:1201-1210 (1998).
Reese et al., "Genie—Gene Finding in *Drosophila melanogaster,*" *Genome Research*, 10:529-538 (2000).
Silverstein et al., "The MetaFam Server: a comprehensive protein family resource," *Nuc. Acids Res.*, 29(1):49-51 (2001).

* cited by examiner

*Primary Examiner*—Marianne P. Allen
(74) *Attorney, Agent, or Firm*—Townsend and Townsend and Crew LLP

(57) ABSTRACT

Methods, software products and systems are provided for automated high throughout gene characterization. In one exemplary embodiment, HMM models are used to characterize genes. Biological sequences are classified according to their hit with different HMM models using a curve analysis.

18 Claims, 10 Drawing Sheets

```
Alignment 1:

1>GRAPAHIT1    1 LLQDSLLRLKDYRQCFECSDVALNEAVQQMVNSGEAAAKEEWVATVTQLL
2>1vhr         1 SVQDLNDLLSDGSGCYSLPSQPCNE VTPRIYVGNASVAQD IPKLQKL 1>GRAPAHIT1   51 MGIEQALSADSSGSILKVSSSTTGLVRLTNNLIQVIDCSMAVQEEAKEPH
2>1vhr        51   GITHVLNAAEGRSFMHVNTNAN 1>GRAPAHIT1  101 VSSVLPWIILHRIIWQEEDTFHSLCHQQQLQNPAEEGMSETPMLPSSLML
2>1vhr       101             FYK            DSGIT 1>GRAPAHIT1  151 LNTAHEYLGRRSWCCNSDGALLRFYVRVLQKELAASTSEDTHPYKEELET
2>1vhr       151     YLGIKA                   NDTQEFN 1>GRAPAHIT1  201 ALEQCFYCLYSFPSKKSKARYLEEHSAQQVDLIWEDALFMFEYFKPKTLP
2>1vhr       201                                        LSAYFERAA 1>GRAPAHIT1  251 EFDSYKTSTVSADLANLLKRIATIVPRTERPALSLDKVSAYIEGTSTEVP
2>1vhr       251 DF         IDQALAQKNGRVL                         VH 1>GRAPAHIT1  301 CLPEGADPSPPVVNELYYLLADYHFKNKEQSKAIKFYMHDICICPNRFDS
2>1vhr       301 C  REGYSRSPTLV    IAYLMMR    QKMDVKSALSIVRQNREIGPN  DG 1>GRAPAHIT1  351 WAGMALARASRIQDKLNSNE LKS
2>1vhr       351 F     LAQLCQLNDRLAKEGKLKP Alignment 2:
1a17              PPADGALKRAEELKTQAN------------DYFKAKDYENAIKFYSQAIE
GRAPAHIT2         PLCKQALEDLEKTSGHDHPDVATMLNILALVYRDQNKYKEAAHLLNDALA
GRAPAHIT3         KDWKGALDAFSAVQDPHSRICFN----IGCMYTILKNMTEAEKAFTRSIN 1a17              L--------NPSNAIYYGNRSLAYLRTECYGYALGDATR-AIELDKKYIK
GRAPAHIT2         IREKTLGKDHPVAATLNNLAVLYGKRGKYKEAEPLCKR-ALEIREKVLG
GRAPAHIT3         R--------DKHLAVAYFQRGMLYYQTEKYDLAIKDLKEALIQLRGNQLI 1a17              GYYRRAASNMA--------LG-------KFRAALRDYET-----------
GRAPAHIT2         KFHPDVAKQLSNLALLCQNQGKAEEVEYYYRRALEIYATRL----GPDDP
GRAPAHIT3         DYKILGLQFKLFACEVLYNIAFMYAKKEEWKKAEEQLALATSMKSEPRHS 1a17              -VVKVKP---------HDKDAKMKYQECNKIVKQKAF-------------
GRAPAHIT2         NVAKTKNNLASCYLKQGKYQDAETLYKEILTRAHEKEFGSVNGDNKPIWM
GRAPAHIT3         KIDKAMECVWKQKLYEPVVIPVGKLFRPNERQVAQLAKKDYLGKATVVAS 1a17              ---ERAIA-----GDEHKR--------SVVDSLDIESMTIEDEYS
GRAPAHIT2         HAEEREES-----KDKRRDSAPYGEYGSWYKACKVDSPTVNTTLR
GRAPAHIT3         VVDQDSFSGFAPLQPQAAEPPPRPKTPEIFRALEGEAHRVLFGFV
```

FIGURE 9

SEQUENCE LISTING

<160> NUMBER OF SEQ ID NOS: 5

<210> SEQ ID NO 1
<211> LENGTH: 373
<212> TYPE: PRT
<213> ORGANISM: Artificial
<220> FEATURE:
<223> OTHER INFORMATION: Protein with similarity to VHR dual specificity phosphatase

<400> SEQUENCE: 1

| Leu | Leu | Gln | Asp | Ser | Leu | Leu | Arg | Leu | Lys | Asp | Tyr | Arg | Gln | Cys | Phe |
|---|---|---|---|---|---|---|---|---|---|---|---|---|---|---|---|
| 1 | | | | 5 | | | | | 10 | | | | | 15 | |

| Glu | Cys | Ser | Asp | Val | Ala | Leu | Asn | Glu | Ala | Val | Gln | Gln | Met | Val | Asn |
|---|---|---|---|---|---|---|---|---|---|---|---|---|---|---|---|
| | | | 20 | | | | | 25 | | | | | 30 | | |

| Ser | Gly | Glu | Ala | Ala | Lys | Glu | Glu | Trp | Val | Ala | Thr | Val | Thr | Gln |
|---|---|---|---|---|---|---|---|---|---|---|---|---|---|---|
| | | 35 | | | | 40 | | | | | 45 | | | |

| Leu | Leu | Met | Gly | Ile | Glu | Gln | Ala | Leu | Ser | Ala | Asp | Ser | Ser | Gly | Ser |
|---|---|---|---|---|---|---|---|---|---|---|---|---|---|---|---|
| | 50 | | | | | 55 | | | | | 60 | | | | |

| Ile | Leu | Lys | Val | Ser | Ser | Thr | Thr | Gly | Leu | Val | Arg | Leu | Thr | Asn |
|---|---|---|---|---|---|---|---|---|---|---|---|---|---|---|
| 65 | | | | | 70 | | | | | 75 | | | | 80 |

| Asn | Leu | Ile | Gln | Val | Ile | Asp | Cys | Ser | Met | Ala | Val | Gln | Glu | Glu | Ala |
|---|---|---|---|---|---|---|---|---|---|---|---|---|---|---|---|
| | | | | 85 | | | | | 90 | | | | | 95 | |

| Lys | Glu | Pro | His | Val | Ser | Ser | Val | Leu | Pro | Trp | Ile | Ile | Leu | His | Arg |
|---|---|---|---|---|---|---|---|---|---|---|---|---|---|---|---|
| | | | 100 | | | | | 105 | | | | | 110 | | |

| Ile | Ile | Trp | Gln | Glu | Glu | Asp | Thr | Phe | His | Ser | Leu | Cys | His | Gln | Gln |
|---|---|---|---|---|---|---|---|---|---|---|---|---|---|---|---|
| | | | 115 | | | | | 120 | | | | | 125 | | |

| Gln | Leu | Gln | Asn | Pro | Ala | Glu | Glu | Gly | Met | Ser | Glu | Thr | Pro | Met | Leu |
|---|---|---|---|---|---|---|---|---|---|---|---|---|---|---|---|
| | 130 | | | | | 135 | | | | | 140 | | | | |

| Pro | Ser | Ser | Leu | Met | Leu | Leu | Asn | Thr | Ala | His | Glu | Tyr | Leu | Gly | Arg |
|---|---|---|---|---|---|---|---|---|---|---|---|---|---|---|---|
| 145 | | | | | 150 | | | | | 155 | | | | | 160 |

| Arg | Ser | Trp | Cys | Cys | Asn | Ser | Asp | Gly | Ala | Leu | Leu | Arg | Phe | Tyr | Val |
|---|---|---|---|---|---|---|---|---|---|---|---|---|---|---|---|
| | | | | 165 | | | | | 170 | | | | | 175 | |

| Arg | Val | Leu | Gln | Lys | Glu | Leu | Ala | Ala | Ser | Thr | Ser | Glu | Asp | Thr | His |
|---|---|---|---|---|---|---|---|---|---|---|---|---|---|---|---|
| | | | 180 | | | | | 185 | | | | | 190 | | |

| Pro | Tyr | Lys | Glu | Glu | Leu | Glu | Thr | Ala | Leu | Glu | Gln | Cys | Phe | Tyr | Cys |
|---|---|---|---|---|---|---|---|---|---|---|---|---|---|---|---|
| | | 195 | | | | | 200 | | | | | 205 | | | |

| Leu | Tyr | Ser | Phe | Pro | Ser | Lys | Lys | Ser | Lys | Ala | Arg | Tyr | Leu | Glu | Glu |
|---|---|---|---|---|---|---|---|---|---|---|---|---|---|---|---|
| | 210 | | | | | 215 | | | | | 220 | | | | |

| His | Ser | Ala | Gln | Gln | Val | Asp | Leu | Ile | Trp | Glu | Asp | Ala | Leu | Phe | Met |
|---|---|---|---|---|---|---|---|---|---|---|---|---|---|---|---|
| 225 | | | | | 230 | | | | | 235 | | | | | 240 |

| Phe | Glu | Tyr | Phe | Lys | Pro | Lys | Thr | Leu | Pro | Glu | Phe | Asp | Ser | Tyr | Lys |
|---|---|---|---|---|---|---|---|---|---|---|---|---|---|---|---|
| | | | | 245 | | | | | 250 | | | | | 255 | |

| Thr | Ser | Thr | Val | Ser | Ala | Asp | Leu | Ala | Asn | Leu | Leu | Lys | Arg | Ile | Ala |
|---|---|---|---|---|---|---|---|---|---|---|---|---|---|---|---|

-continued

```
                    260                 265                 270
Thr Ile Val Pro Arg Thr Glu Arg Pro Ala Leu Ser Leu Asp Lys Val
            275                 280                 285

Ser Ala Tyr Ile Glu Gly Thr Ser Thr Glu Val Pro Cys Leu Pro Glu
        290                 295                 300

Gly Ala Asp Pro Ser Pro Pro Val Val Asn Glu Leu Tyr Tyr Leu Leu
305                 310                 315                 320

Ala Asp Tyr His Phe Lys Asn Lys Glu Gln Ser Lys Ala Ile Lys Phe
                325                 330                 335

Tyr Met His Asp Ile Cys Ile Cys Pro Asn Arg Phe Asp Ser Trp Ala
            340                 345                 350

Gly Met Ala Leu Ala Arg Ala Ser Arg Ile Gln Asp Lys Leu Asn Ser
        355                 360                 365

Asn Glu Leu Lys Ser
        370
```

<210> SEQ ID NO 2
<211> LENGTH: 178
<212> TYPE: PRT
<213> ORGANISM: Artificial
<220> FEATURE:
<223> OTHER INFORMATION: VHR dual specificity phosphatase

<400> SEQUENCE: 2

```
Ser Val Gln Asp Leu Asn Asp Leu Leu Ser Asp Gly Ser Gly Cys Tyr
1               5                   10                  15

Ser Leu Pro Ser Gln Pro Cys Asn Glu Val Thr Pro Arg Ile Tyr Val
            20                  25                  30

Gly Asn Ala Ser Val Ala Gln Asp Ile Pro Lys Leu Gln Lys Leu Gly
        35                  40                  45

Ile Thr His Val Leu Asn Ala Ala Glu Gly Arg Ser Phe Met His Val
    50                  55                  60

Asn Thr Asn Ala Asn Phe Tyr Lys Asp Ser Gly Ile Thr Tyr Leu Gly
65                  70                  75                  80

Ile Lys Ala Asn Asp Thr Gln Glu Phe Asn Leu Ser Ala Tyr Phe Glu
                85                  90                  95

Arg Ala Ala Asp Phe Ile Asp Gln Ala Leu Ala Gln Lys Asn Gly Arg
            100                 105                 110

Val Leu Val His Cys Arg Glu Gly Tyr Ser Arg Ser Pro Thr Leu Val
        115                 120                 125

Ile Ala Tyr Leu Met Met Arg Gln Lys Met Asp Val Lys Ser Ala Leu
    130                 135                 140

Ser Ile Val Arg Gln Asn Arg Glu Ile Gly Pro Asn Asp Gly Phe Leu
145                 150                 155                 160

Ala Gln Leu Cys Gln Leu Asn Asp Arg Leu Ala Lys Glu Gly Lys Leu
                165                 170                 175

Lys Pro
```

<210> SEQ ID NO 3
<211> LENGTH: 159
<212> TYPE: PRT
<213> ORGANISM: Artificial
<220> FEATURE:
<223> OTHER INFORMATION: Protein phosphatase 5

<400> SEQUENCE: 3

Pro Pro Ala Asp Gly Ala Leu Lys Arg Ala Glu Glu Leu Lys Thr Gln

```
  1               5                   10                  15
Ala Asn Asp Tyr Phe Lys Ala Lys Asp Tyr Glu Asn Ala Ile Lys Phe
                 20                  25                  30

Tyr Ser Gln Ala Ile Glu Leu Asn Pro Ser Asn Ala Ile Tyr Tyr Gly
                 35                  40                  45

Asn Arg Ser Leu Ala Tyr Leu Arg Thr Glu Cys Tyr Gly Tyr Ala Leu
                 50                  55                  60

Gly Asp Ala Thr Arg Ala Ile Glu Leu Asp Lys Lys Tyr Ile Lys Gly
 65                  70                  75                  80

Tyr Tyr Arg Arg Ala Ala Ser Asn Met Ala Leu Gly Lys Phe Arg Ala
                 85                  90                  95

Ala Leu Arg Asp Tyr Glu Thr Val Val Lys Val Lys Pro His Asp Lys
                 100                 105                 110

Asp Ala Lys Met Lys Tyr Gln Glu Cys Asn Lys Ile Val Lys Gln Lys
                 115                 120                 125

Ala Phe Glu Arg Ala Ile Ala Gly Asp Glu His Lys Arg Ser Val Val
                 130                 135                 140

Asp Ser Leu Asp Ile Glu Ser Met Thr Ile Glu Asp Glu Tyr Ser
145                 150                 155

<210> SEQ ID NO 4
<211> LENGTH: 235
<212> TYPE: PRT
<213> ORGANISM: Artificial
<220> FEATURE:
<223> OTHER INFORMATION: Protein with protein phosphatase 5 fold

<400> SEQUENCE: 4

Pro Leu Cys Lys Gln Ala Leu Glu Asp Leu Glu Lys Thr Ser Gly His
 1               5                   10                  15

Asp His Pro Asp Val Ala Thr Met Leu Asn Ile Leu Ala Leu Val Tyr
                 20                  25                  30

Arg Asp Gln Asn Lys Tyr Lys Glu Ala Ala His Leu Leu Asn Asp Ala
                 35                  40                  45

Leu Ala Ile Arg Glu Lys Thr Leu Gly Lys Asp His Pro Ala Val Ala
 50                  55                  60

Ala Thr Leu Asn Asn Leu Ala Val Leu Tyr Gly Lys Arg Gly Lys Tyr
 65                  70                  75                  80

Lys Glu Ala Glu Pro Leu Cys Lys Arg Ala Leu Glu Ile Arg Glu Lys
                 85                  90                  95

Val Leu Gly Lys Phe His Pro Asp Val Ala Lys Gln Leu Ser Asn Leu
                 100                 105                 110

Ala Leu Leu Cys Gln Asn Gln Gly Lys Ala Glu Glu Val Glu Tyr Tyr
                 115                 120                 125

Tyr Arg Arg Ala Leu Glu Ile Tyr Ala Thr Arg Leu Gly Pro Asp Asp
                 130                 135                 140

Pro Asn Val Ala Lys Thr Lys Asn Asn Leu Ala Ser Cys Tyr Leu Lys
145                 150                 155                 160
```

```
Gln Gly Lys Tyr Gln Asp Ala Glu Thr Leu Tyr Lys Glu Ile Leu Thr
                165                 170                 175

Arg Ala His Glu Lys Glu Phe Gly Ser Val Asn Gly Asp Asn Lys Pro
            180                 185                 190

Ile Trp Met His Ala Glu Arg Glu Glu Ser Lys Asp Lys Arg Arg
            195                 200                 205

Asp Ser Ala Pro Tyr Gly Glu Tyr Gly Ser Trp Tyr Lys Ala Cys Lys
        210                 215                 220

Val Asp Ser Pro Thr Val Asn Thr Thr Leu Arg
225                 230                 235

<210> SEQ ID NO 5
<211> LENGTH: 233
<212> TYPE: PRT
<213> ORGANISM: Artificial
<220> FEATURE:
<223> OTHER INFORMATION: Protein with protein phosphatase 5 fold

<400> SEQUENCE: 5

Lys Asp Trp Lys Gly Ala Leu Asp Ala Phe Ser Ala Val Gln Asp Pro
1               5                   10                  15

His Ser Arg Ile Cys Phe Asn Ile Gly Cys Met Tyr Thr Ile Leu Lys
            20                  25                  30

Asn Met Thr Glu Ala Glu Lys Ala Phe Thr Arg Ser Ile Asn Arg Asp
        35                  40                  45

Lys His Leu Ala Val Ala Tyr Phe Gln Arg Gly Met Leu Tyr Tyr Gln
    50                  55                  60

Thr Glu Lys Tyr Asp Leu Ala Ile Lys Asp Leu Lys Glu Ala Leu Ile
65                  70                  75                  80

Gln Leu Arg Gly Asn Gln Leu Ile Asp Tyr Lys Ile Leu Gly Leu Gln
                85                  90                  95

Phe Lys Leu Phe Ala Cys Glu Val Leu Tyr Asn Ile Ala Phe Met Tyr
            100                 105                 110

Ala Lys Lys Glu Glu Trp Lys Lys Ala Glu Glu Gln Leu Ala Leu Ala
        115                 120                 125

Thr Ser Met Lys Ser Glu Pro Arg His Ser Lys Ile Asp Lys Ala Met
    130                 135                 140

Glu Cys Val Trp Lys Gln Lys Leu Tyr Glu Pro Val Val Ile Pro Val
145                 150                 155                 160

Gly Lys Leu Phe Arg Pro Asn Glu Arg Gln Val Ala Gln Leu Ala Lys
                165                 170                 175

Lys Asp Tyr Leu Gly Lys Ala Thr Val Val Ala Ser Val Val Asp Gln
            180                 185                 190

Asp Ser Phe Ser Gly Phe Ala Pro Leu Gln Pro Gln Ala Ala Glu Pro
        195                 200                 205

Pro Pro Arg Pro Lys Thr Pro Glu Ile Phe Arg Ala Leu Glu Gly Glu
    210                 215                 220

Ala His Arg Val Leu Phe Gly Phe Val
225                 230
```

COMPUTER SOFTWARE FOR AUTOMATED ANNOTATION OF BIOLOGICAL SEQUENCES

CROSS REFERENCE TO RELATED APPLICATIONS

Referenced-applications

This application claims the priority of U.S. Provisional Application Nos. 60/285,144, filed on Apr. 19, 2001 and 60/285,403, filed on Apr. 20, 2001. The 60/285,144 and 60/285,403 applications are incorporated herein by reference for all purposes.

COPYRIGHT STATEMENT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies to the software and data as described below and in the drawing hereto: Copyright 2001, Affymetrix, Inc. All Rights Reserved.

BACKGROUND OF INVENTION

The present invention relates to bioinformatics and biological computing. More specifically, embodiments of the invention provides methods, systems and computer software for annotating biological sequences.

In recent years, the growth of the genomic databases has been explosive. With the recent completion of the human genome and the upcoming mouse genome, this growth is likely to continue. This explosion of data has highlighted the need for accurate, high-throughput methods for gene characterization.

SUMMARY OF INVENTION

Methods, computer software and systems are provided for highly accurate and automated gene characterization. The methods, computer software and system of the invention can be used to assign genes to families based upon protein (domain) structural similarity.

In one aspect of the invention, methods, software and systems are provided for automated threshold (cutoff) analysis. The methods, software and systems are particularly suitable for automated gene annotation/characterization. In some embodiments of the invention, curve analysis is used to process Hidden Markov Model (HMM) scores, independent of the HMM properties.

Some embodiments of the computer implemented methods of the invention include the steps of obtaining a plurality of models (such as a battery of HMMs), where each of the models represents a classification of biological sequences with structural or functional similarity; determining distances of the biological sequences to the models; and automatically classifying the sequences according to the distances to the models. The methods are particularly suitable for annotating a large number of sequences, preferably at least 50, 100, 500, 1000, or 5000 sequences. In preferred embodiments, the sequences are protein sequences. In such embodiments, the models are typically established according to structural relationships among known proteins. Data from many protein databases, such as the Structural Classification of Proteins (SCOP) World Wide Web Address: scop.berkeley.edu) and Protein Data Bank (PDB) World Wide Web Address: www.rcsb.org/pdb/) are useful for building the HMM libraries in at least some embodiments of the invention.

In one preferred embodiment, the computer implemented method for gene characterization include generating libraries of models (such as the hidden markov models) using structural relationships of known proteins; inputting a plurality of protein sequences;comparing the plurality of protein sequences with the models; automatically establishing criteria for assigning the sequences for each model; and assigning the sequences to the models based upon the criteria.

In some instances, nucleic acid sequences are characterized by first translating the coding regions of the nucleic acid sequences into peptide sequences. In some preferred embodiments, genes are predicted genomic sequences, such as the human genome sequences. The genes are then translated and characterized at the protein level. In preferred embodiments, at least 50, 100, 500, 1000, or 5000 predicted genes are annotated.

In another aspect of the invention, systems and computer software are provided for performing the methods of the invention. The systems include a processor; and a memory coupled with the processor, the memory storing a plurality of machine instructions that cause the processor to perform logical steps of the methods of the invention. The computer software products of the invention include a computer readable medium having computer-executable instructions for performing the methods of the invention.

BRIEF DESCRIPTION OF DRAWINGS

The accompanying drawings, which are incorporated in and form a part of this specification, illustrate embodiments of the invention and, together with the description, serve to explain the principles of the invention:

FIG. 9 shows phosphatase alignments (SEQ ID NOS: 1–5).

DETAILED DESCRIPTION

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention.

The present invention provides computational methods, computer software products and systems for rapid automatic characterization of genes. While the invention will be primarily described using protein analysis as exemplary embodiments of the invention, this invention is not limited to protein analysis.

All patents and publications are herein incorporated by reference to the same extent as if each individual publication was specifically and individually indicated to be incorporated by reference.

Systems and Software for High Throughput Automated Gene Characterization

In aspects of the invention, methods, computer software and systems for gene characterization are provided. Systems of the invention typically include one or more processing units and a coupled memory for executing the software of the invention or otherwise executing logic steps of the methods of the invention. One of skill in the art would appreciate that computer software according to the embodiments of the invention can be executed in a wide variety of computer systems.

For a description of basic computer systems and computer networks, see, e.g., Introduction to Computing Systems: From Bits and Gates to C and Beyond by Yale N. Patt, Sanjay J. Patel, 1st edition (Jan. 15, 2000) McGraw Hill Text; ISBN: 0072376902; and Introduction to Client/Server Systems: A Practical Guide for Systems Professionals by Paul E. Renaud, 2nd edition (June 1996), John Wiley & Sons; ISBN: 0471133337, both are incorporated herein by reference in their entireties for all purposes.

Figure 1:
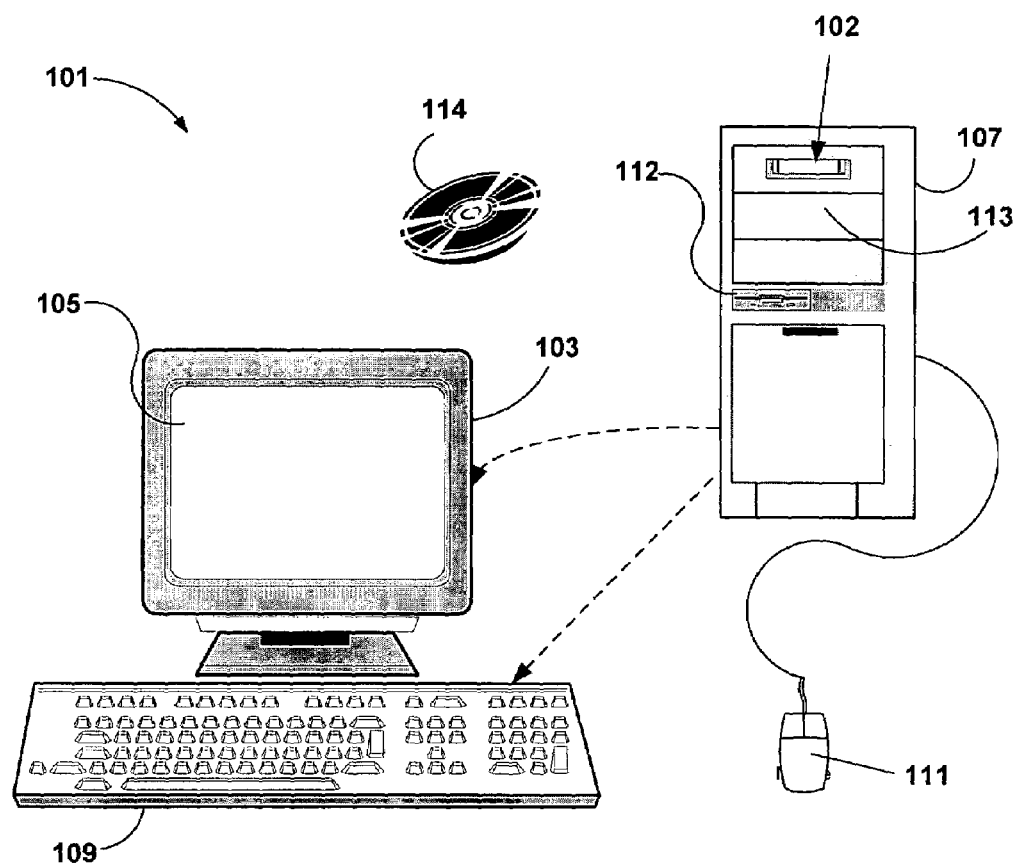
FIG. 1 is a schematic showing an exemplary computer system suitable for executing some embodiments of the software of the invention.

FIG. 1 illustrates an exemplary computer system that may be used to execute the software of an embodiment of the invention. FIG. 1 shows a computer system 101 that includes a display 103, screen 105, cabinet 107, keyboard 109, and mouse 111. Mouse 111 may have one or more buttons for interacting with a graphic user interface. Cabinet 107 houses a floppy drive 112, CD-ROM or DVD-ROM drive 102, system memory and a hard drive (113) (see also FIG. 2) which may be utilized to store and retrieve software programs incorporating computer code that implements the invention, data for use with the invention and the like. Although a CD 114 is shown as an exemplary computer readable medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
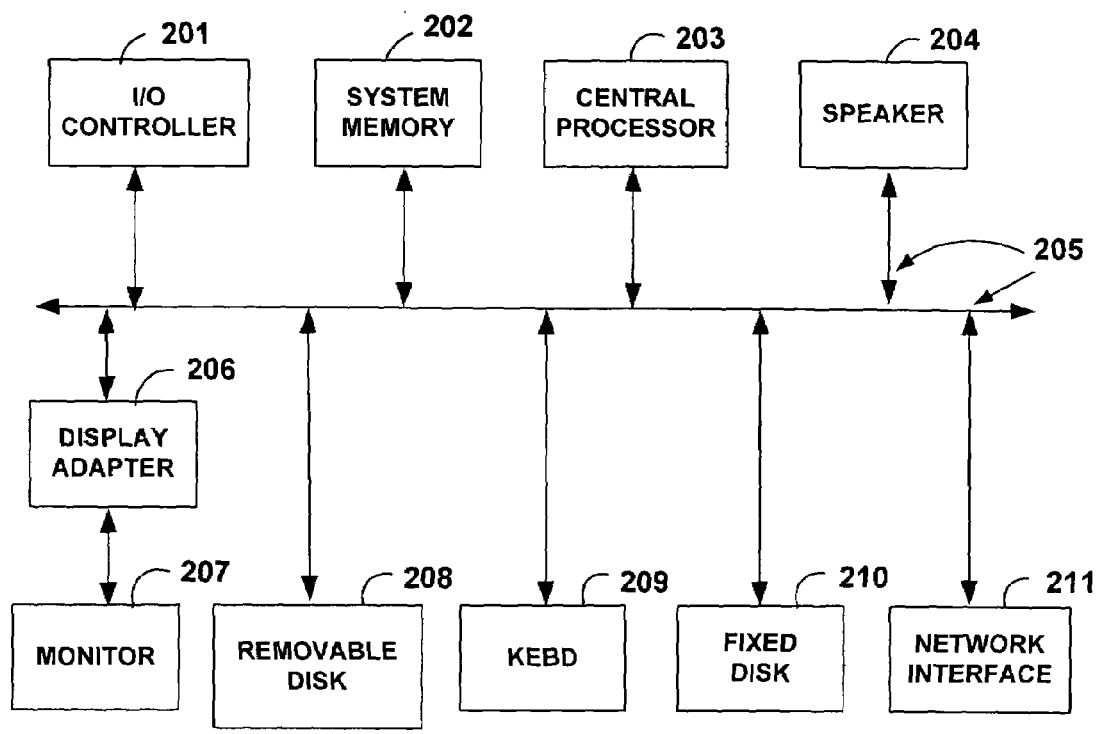
FIG. 2 is a schematic showing the architecture of the exemplary computer system of FIG. 1.

FIG. 2 shows a system block diagram of computer system 101 used to execute the software of an embodiment of the invention. As in FIG. 1, computer system 101 includes monitor 201, and keyboard 209. Computer system 101 further includes subsystems such as a central processor 203 (such as a Pentium™ III processor from Intel), system memory 202, fixed storage 210 (e.g., hard drive), removable storage 208 (e.g., floppy or CD-ROM), display adapter 206, speakers 204, and network interface 211. Other computer systems suitable for use with the invention may include additional or fewer subsystems. For example, another computer system may include more than one processor 203 or a cache memory. Computer systems suitable for use with the invention may also be embedded in a measurement instrument.

Figure 3:
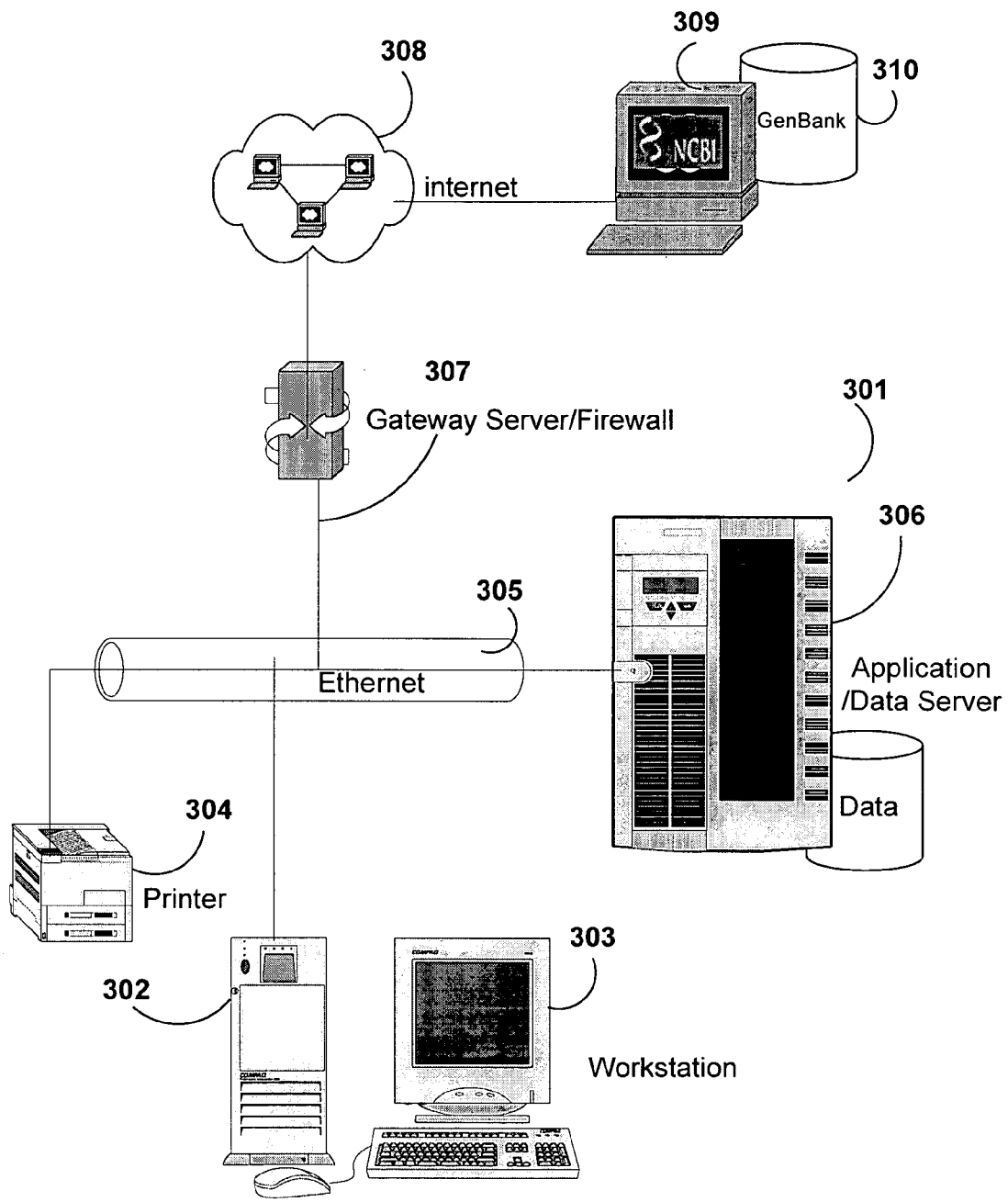
FIG. 3 shows an exemplary computer network system suitable for executing some embodiments of the software of the invention.

FIG. 3 shows an exemplary computer network that is suitable for executing the computer software of the invention. A computer workstation 302 is connected with the application/data server(s) through a local area network (LAN) 301, such as an Ethernet 305. A printer 304 may be connected directly to the workstation or to the Ethernet 305. The LAN may be connected to a wide area network (WAN), such as the Internet 308, via a gateway server 307 which may also serve as a firewall between the WAN 308 and the LAN 305. In preferred embodiments, the workstation may communicate with outside data sources, such as the National Biotechnology Information Center, through the Internet. Various protocols, such as FTP and HTTP, may be used for data communication between the workstation and the outside data sources. Outside genetic data sources, such as the GenBank 310, are well known to those skilled in the art. An overview of GenBank and the National Center for Biotechnology information (NCBI) can be found in the web site of NCBI World Wide Web Address: www.ncbi.nlm.nih.gov). Other useful Internet accessible databases include Structural Classification of Proteins (SCOP) World Wide Web Address: scop.berkeley.edu) and Protein Data Bank (PDB) World Wide Web Address: www.rcsb.org/pdb/). Additional biological databases accessible through the internet are described in, e.g., Special Issue on Biological Databases, Nucleic Acid Research, 2000, 29:0–349, incorporated herein in its entirety by reference for all purposes. Protein databases are also discussed in Section II, infra.

Computer software products of the invention typically include computer readable medium having computer-executable instructions for performing the logic steps of the methods of the invention. Suitable computer readable medium include floppy disk, CD-ROM/DVD/DVD-ROM, hard-disk drive, flash memory, ROMIRAM, magnetic tapes and etc. The computer executable instructions may be written in any suitable computer language or combination of several languages. Suitable computer languages include C##, C/C++ (such as Visual C/C++), Java, Basic (such as Microsoft Visual Basic), SQL, Fortran, SAS and Perl. The software may be written in the form of independent software, software components (such as Java beans, Enterprise Java Beans). Software of the invention may also be implemented to provide application programming interfaces (APIs). In preferred embodiments, the software of the invention may provide remote services using remote execution in a distribute fashion. For example, in some embodiments, some or all of the logic steps of the methods and software of the invention are implemented as Web Services. For a detailed description of Web Services, see, e.g., "Web Services Insider," by James Snell, available at: World Wide Web Address: www-106.ibm.com/developerworks/webservices/library/we-refl.html, last visited Sep. 20, 2001.

Protein Databases

The well-characterized proteins in the Protein Database (PDB) have been studied at sequence, structure, and function levels, providing a richer description than the sequence-level information one finds in GenBank. As a result, these database entries are closely studied by scientists interested in protein folding, drug design, protein-protein interaction elucidation, evolutionary context, and gene annotation. In some aspects of the invention, protein databases are employed for rapid automated gene characterization. Some exemplary databases suitable for use with the methods of the invention are described in this section.

Most, if not all proteins, have some structural similarities with other proteins, often as a result of a common evolutionary origin. The Structural Classification of Proteins (SCOP) (Murzin, A., Brenner, S. E, Hubbard, T. Chothia, C., 1995. SCOP: A Structural Classification of Proteins Database for the Investigation of Sequences and Structures. J. Mol. Biol., 247:536–540, incorporated herein by reference in its entirety for all purposes) scheme categorizes all the domains in the PDB into a hierarchy based on their structural and evolutionary proximity. The SCOP database provides a comprehensive description of the structural and evolutionary relationships between all proteins whose structure is known, including all entries in the Protein Data Bank (PDB).

The SCOP classification of proteins is constructed manually by visual inspection and comparison of structures with the assistance of computational tools. Proteins are classified according to their structural and evolutionary relationship. Many levels exist in the hierarchy, but the principal levels are family, superfamily and fold.

In the SCOP scheme, proteins clustered into families are clearly evolutionarily related. Generally, this means that pairwise residue identities between the proteins are 30% and greater. However, in some cases similar functions and structures provide definitive evidence of common descent in the absense of high sequence identity; for example, many globins form a family though some members have sequence identities of only 15%.

Proteins that have low sequence identities, but whose structural and functional features suggest that a common evolutionary origin is probable are placed together in superfamilies. For example, actin, the ATPase domain of the heat shock protein, and hexakinase together form a superfamily.

Proteins are defined as having a common fold if they have the same major secondary structures in the same arrangement and with the same topological connections. Different proteins with the same fold often have peripheral elements of secondary structure and turn regions that differ in size and conformation. In some cases, these differing peripheral regions may comprise half the structure. Proteins placed together in the same fold category may not have a common evolutionary origin: the structural similarities could arise just from the physics and chemistry of proteins favoring certain packing arrangements and chain topologies.

Protein Information Resource (PIR) is another database with protein classifications. See, e.g., Barker et al., (2001). Protein Information Resource: a community resource for expert annotation of protein data. Nucleic Acids Research, 29, 29–32. In the PIR scheme, database entries are organized into families of closely related sequences. These generally represent proteins with the same function in various organisms.

Generalized Rapid Automated Protein Analysis

Many functionally and evolutionarily important protein similarities can be analyzed by comparing three-dimensional structures. When such structures are not available, patterns of conservation identified from the alignment of related sequences can be used to discover distant similarities (homology detection).

Iterative profile search methods are the most widely-used family of homology detection methods. This family of methods includes PSI-BLAST (Altschul, Madden et al. 1997, Gapped BLAST and PSI-BLAST: a new generation of protein database search programs. Nucleic Acids Res 25(17), 3389–402.), SAM-T99 (Karplus, Barrett et al. 1998, Hidden Markov models for detecting remote protein homologies. Bioinformatics 14(10), 846–56.), and Pfam (Bateman, Birney et al. 2000, The Pfam protein families database. Nucleic Acids Res 28(1), 263–6.). They are more sensitive than comparisons of single sequences, detecting as many as three times the number of remote homologs as pairwise comparison methods (Park, Karplus et al. 1998, Sequence comparisons using multiple sequences detect three times as many remote homologues as pairwise methods. J Mol Biol 284(4), 1201–10.). They require no structural information, making them viable when structural information is limited. Finally, they are relatively easy to automate, and efficient enough to make them feasible for large-scale efforts such as whole-genome annotation. There are a variety of such methods. PSI-BLAST iteratively builds a statistical profile of the query sequence and homologs on the fly as it searches for other homologs, matching the profile. GRAPA (using SAM-T99) and Pfam (using HMMR) both compare the query sequence to pre-computed HMMs based on hand-curated family alignments in Pfam, and automatically-generated superfamily alignments in SAM-T99. While these methods search according to domain-wide conservation patterns, meta-MEME (Grundy, Bailey et al. 1997, Meta-MEME: motif-based hidden Markov models of protein families. Comput Appl Biosci 13(4), 397–406.) searches according to patterns of highly-represented motifs. Other methods, such as FORESST (Geetha, Di Francesco et al. 1999, Comparing protein sequence-based and predicted secondary structure-based methods for identification of remote homologs. Protein Eng 12(7), 527–34.) ssHMM (Hargbo and Elofsson 1999, Hidden Markov models that use predicted secondary structures for fold recognition. Proteins 36(1), 68–76.) search for homology according to comparisons of secondary structure rather than purely sequence-based comparisons. MetaFam (Silverstein, Shoop et al. 2001, The MetaFam Server: a comprehensive protein family resource. Nucleic Acids Res 29(1), 49–51.) and Interpro (Apweiler, Attwood et al. 2001, The InterPro database, an integrated documentation resource for protein families, domains and functional sites. Nucleic Acids Res 29(1), 37–40.) provide meta-searches combining the results of multiple methods.

In one aspect of the invention, methods, software and systems are provided for using a high-accuracy system of hidden Markov models (HMMs) for automated genome annotation. Proteins are annotated by competing batteries of HMMs to yield family designations. This HMM library is applied to exploring uncharacterized genes. The Generalized Rapid Automated Protein Analysis (GRAPA) system assesses annotation significance with a dynamic cutoff, which compensates for the variance in the quality of distance calculations from one HMM to another.

GRAPA's foundation is a battery of Hidden Markov Models (HMMs) automatically generated to detect a protein's nearest family from the Structural Classification of Proteins (SCOP) hierarchy (Murzin, Brenner et al. 1995, SCOP: a structural of proteins database for the investigation of sequences and structures. J Mol Biol 247 (4), 536–40), a categorization of the Protein Data Bank (PDB) (Berman, Westbrook et al. 2000, The Protein Data Bank. Nucleic Acids Res 28(1), 235–42.).

GRAPA has an estimated false positive rate of only 5.7%, with a false negative rate of only 22.8%. While exemplary embodiments of GRAPA is based on the SCOP hierarchy, the method requires no structural information, and is applicable to cases where structural information is limited such as transmembrane proteins. As demonstrated by detailed analysis of phosphatase protein categories, GRAPA finds roughly three times as many significant sequences from a non-redundant set of human genes as BLASTP. PSI-BLAST has a comparable selectivity, but yields 20% fewer high quality putative phosphatases when compared to GRAPA. Given these properties, GRAPA gives researchers access to a highly sensitive homology-derived functional database for classifying genes and determining gene function.

In contrast to other gene characterization applications, GRAPA uses clusters of broadly trained HMMs. In contrast to annotation schemes which use a single HMM to identify the family or the superfamily of a protein, GRAPA uses an HMM based on each SCOP family member which incorporates a broad range of homologous proteins, comparable to those used to identify a protein superfamily. This gives the HMM a broader range of coverage in sequence space than a PSI-BLAST profile, while still allowing GRAPA to assign a protein family to each candidate. As illustrated in FIG. 3, a protein sequence is assigned to a SCOP family by comparing the distance scores of each candidate for each of the HMMs in the superfamily group. While GRAPA's HMMs do not always present a broader search in sequence space, they should usually present more results than a profile generated by the approach used by programs like PSI-BLAST.

In preferred embodiments, the SAM-T99 or similar systems are used. In blind experiments in the CASP contests, the SAM-T99 HMM system (Karplus, Barrett et al. 1998) has been shown consistently to be one of the best homology recognition systems that require no structural information (Karplus, Sjolander et al. 1997; Karplus, Barrett et al. 1999; Karplus, Karchin et al. 2001). In a recent investigation of family, superfamily, and fold level homology recognition, HMMs were the most successful method for family-level recognition (Lindahl and Elofsson 2000). Starting with this seed sequence or alignment, a model is built in an iterative fashion, the model used to search for additional homologs, and reestimates the alignment with the new homologs. HMMs are among the best homology recognition tools available at this time.

Figure 4:
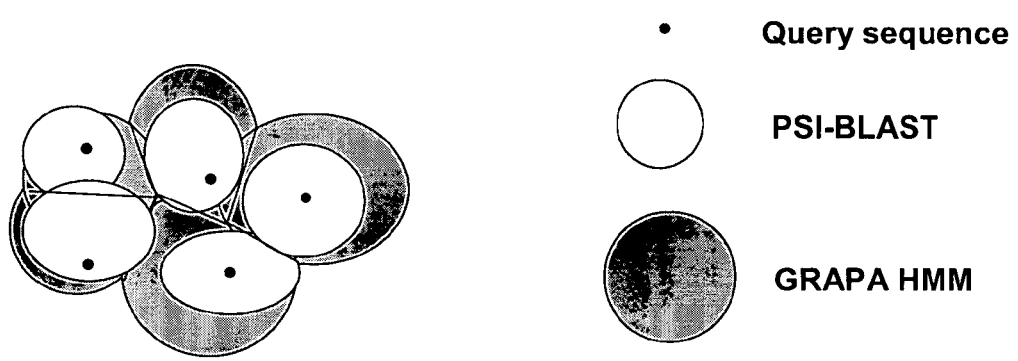
FIG. 4 illustrates GRAPA Scheme.

As FIG. 4 shows, HMMs (dark areas) have a wider range in sequence space than PSI-BLAST (light area), from the query (seed) sequences (dark points). The HMM candidates are then sorted into their most likely family (sorting represented by the black lines). This enables GRAPA to cover a larger region of sequence space while still giving family information.

SAM-T99 was designed for protein structure prediction, and optimized for recognizing proteins of common structure (superfamily recognition). Gough et al. (Gough, Chothia et al. 2000, Optimal Hidden Markov Models for All Sequences of Known Structure. Currents in Computational Molecular Biology 2000) provide Superfamily, a web-based service, which uses HMMs built around SCOP seed sequences with SAM-T99 default settings for superfamily recognition. Superfamily is meant as a service for superfamily identification of sequences submitted to the web-site.

Generally, sequence can be compared to a model by calculating the probability that the sequence was generated by that model. For SAM-T99, the negative (natural) logarithm of this probability gives the NLL score. However, the NLL score has a strong dependence on sequence length and model length. The SAM-T99 Hmmscore program provides several less biased means of scoring by reporting NLL scores as the difference between a null model and trained model NLL score (a log-odds score, as used in HMMER).

Null model scoring is discussed in more detail in Hughey Christian Barrett, Richard Hughey, and Kevin Karplus, 1997, Scoring Hidden Markov Models, CABIOS 13(2): 191–199, incorporated herein by reference. This paper is also available at the following URL (www.cse.ucsc.edu/research/compbio/papers/nullmod/nullmod.html), last visited on Sep. 20, 2001. The E-value is the expected number of sequences with a particular score. For methods of calculating the E-value, see, e.g., Richard Hughey—Kevin Karplus—Anders Krogh, SAM Sequence Alignment and Modeling Software System, Baskin Center for Computer Engineering and Science, University of California Santa Cruz, Calif. 95064, Technical Report UCSC-CRL-99-11, Updated for SAM Version 3.2, Jul. 31, 2000, incorporated herein by reference. This document is also available at the following URL (www.cse.ucsc.edu/research/compbio/papers/sam_doc/sam_doc.html, last visited on Sep. 20, 2001).

Many of the SCOP HMMs (4,369 models built for SCOP v.1.53) exhibit a lack of consistency in HMM scoring, expressed as an E-value probability. Since scoring is dependent upon sequence length and the significance of specific amino acid positions, there has not been any automated scoring of HMMbased annotation systems for high throughput annotation. Instead, SAM-99 provides a set of tools for various plot scores. SAM-T99 recommends that plots of the scores be used to visually look for a break between significant and insignificant matches. The visualization examination, while effective in handling small set of models, are not practical for handling a large number of models in a high throughput environment.

Figure 5:
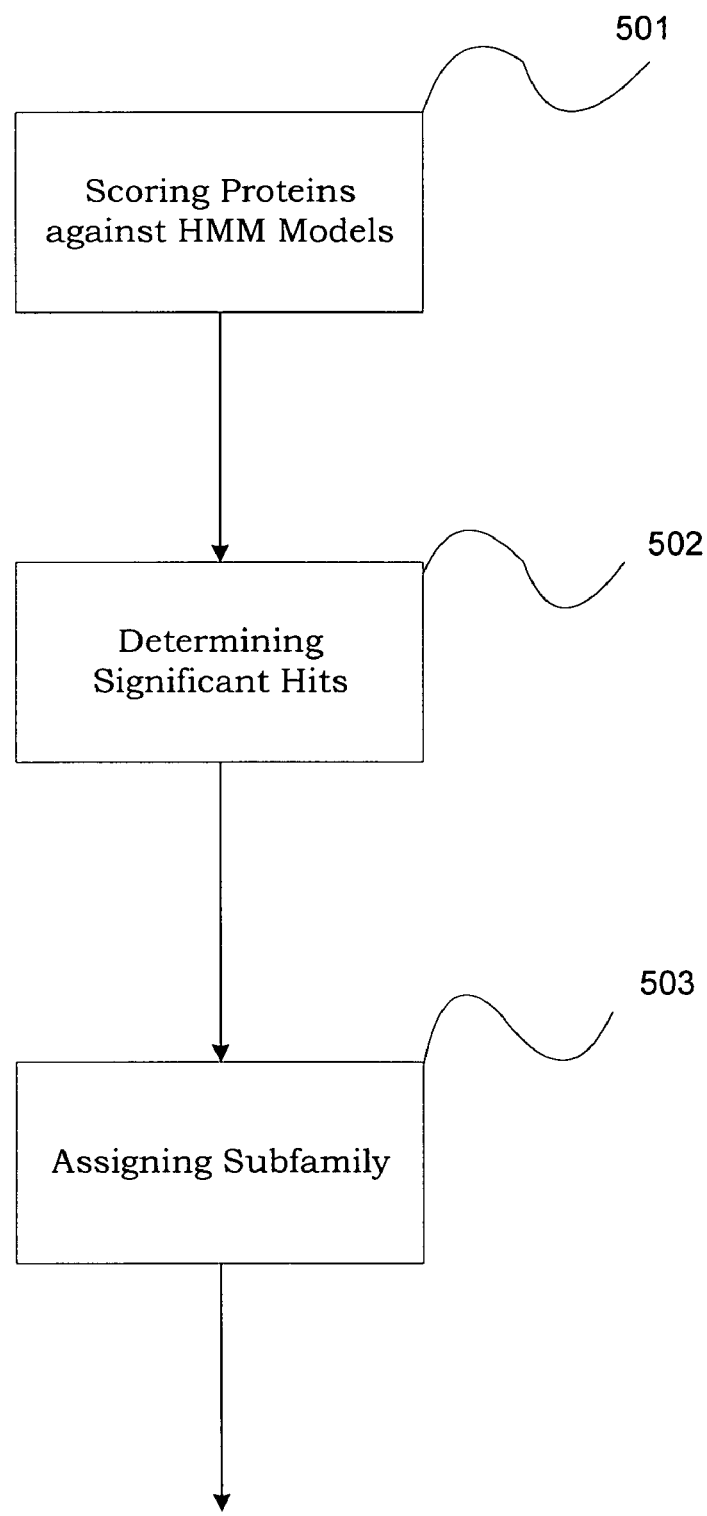
FIG. 5 shows an automated process for characterizing a protein sequence.

In one aspect of the invention, methods, software and systems are provided for automated threshold (cutoff) analysis. The methods, software and systems are particularly suitable for automated gene annotation/characterization. FIG. 5 illustrates an embodiment of the process. Candidate proteins are scored against HMM models (501). The scores are analyzed to determine significant hits (502). The proteins are then assigned into subfamily according to the hits to the models (503).

Figure 6:
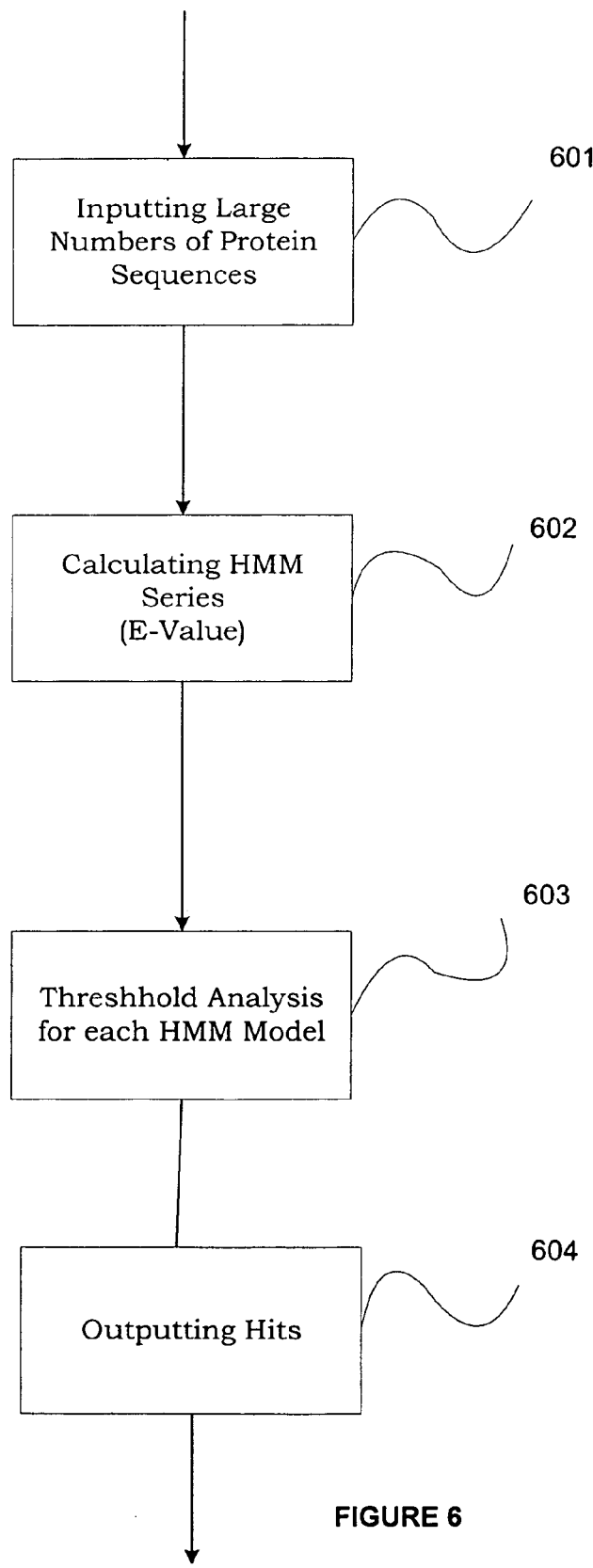
FIG. 6 shows process for automated process for annotating protein sequences using HMM models.
Figure 7:
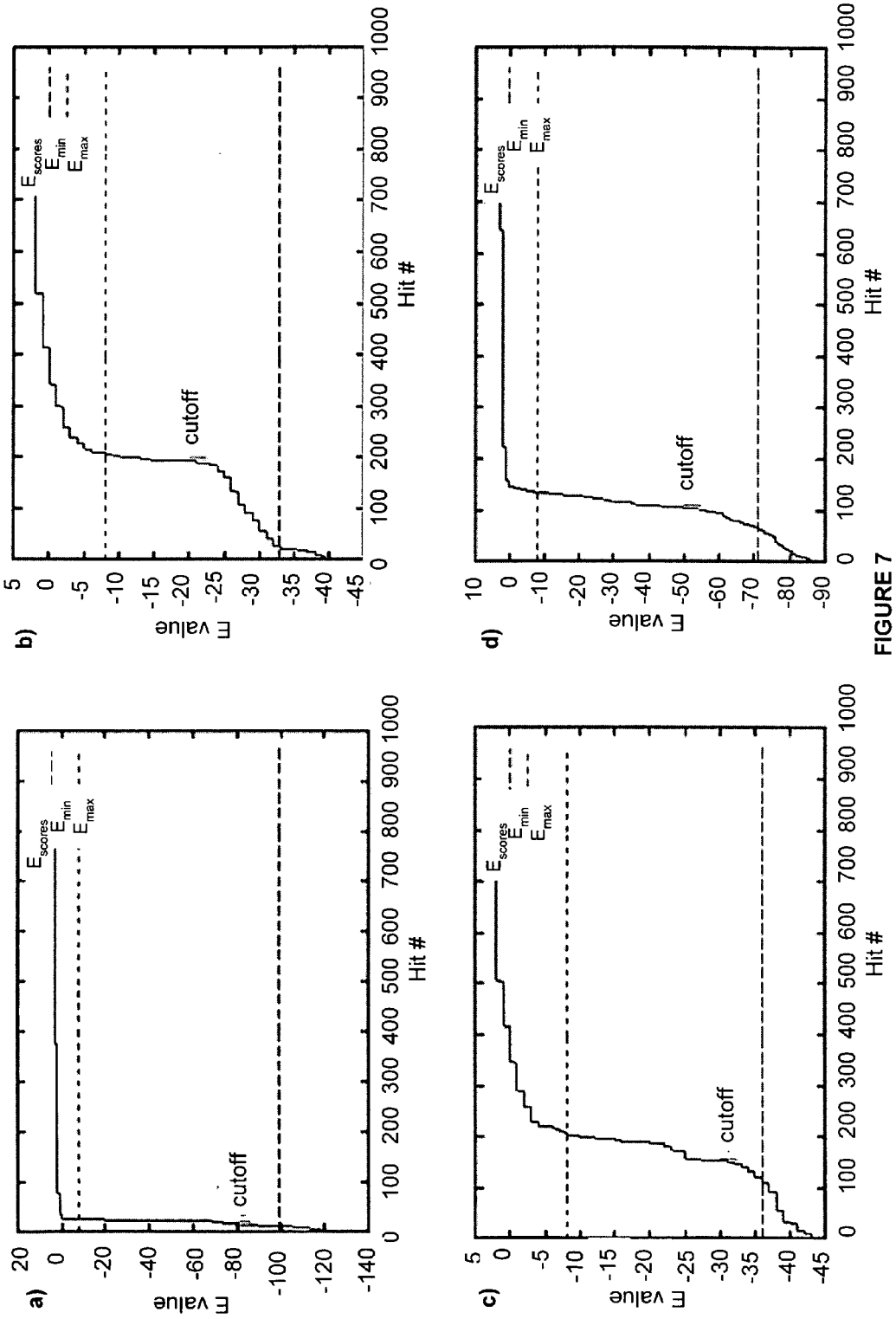
FIG. 7a–d depicts HMM score E-values verses sorted hits.

In preferred embodiments, automated threshold analysis is used to distinguish between hits and non-hits, allowing the results for each HMM to be analyzed in an unsupervised annotation. FIG. 6 shows a process for threshold analysis. A large number of protein sequences, for example, at least 5, 10, 50, 100, 500, 1000, 5000, protein sequences are inputted (601) and scored for a large number of HMMs (602). The resulting score (E-value) is analyzed for hits (603). The hits are outputted (604).

In preferred embodiments, the threshold analysis is performed with a curve analysis. In a particularly preferred embodiment, five criteria are used to distinguish the hits to be kept: (1) when the E-values rise above a value of e-05 they are discarded regardless of the other criteria; (2) the first ten hits are kept provided they score better than e-05; (3) the hits more than 70% of the log of the maximum score are automatically kept; (4) the point where the E-value plot drops abruptly or flattens is used as a threshold; (5) no more than a maximum number of hits (e.g., 1000) are kept.

An exemplary PERL script for performing one embodiment of the curve analysis is provided in the computer program listing.

FIGS. 7a–d show four example graphs depicting HMM score E-values verses sorted hits. The shoulder where the E-values drop off abruptly or the curve flattens is used to determine where to cut off assignment to the family, denoted by small vertical bar. These curves are chosen to illustrate the variability of slopes and E-value ranges among the 4369

HMMs representing SCOP. HMM 20 (hemoglobin, alpha-chain, 1hbr) shows only approximately 30 hits with E-values in the e-60 to e45 range. Below e-45, E-values drop off abruptly. The threshold detection algorithm identifies the threshold, in a second steep drop at approximately e-25. HMM 857 (immunoglobulin variable domains of L chain, 1 afv) shows a large number of hits in the e-50 to e-30 range, which drops off abruptly after approximately 160 hits. Note that a double shoulder is found such that a related set of proteins in the 160–190 range might be considered in other circumstances. HMM 1702 (Thrombin, 1702) shows a very gradual falling off of E-value over the first 100 hits. The threshold finding algorithm succeeds in detecting the start of the steep drop-off in E-value; hand-tuning of this threshold might be useful in subjectively determining what proteins are truly members of this family. HMM 1765 (pepsinogen, 1 pso) depicts a set of proteins, with very few high-quality hits; however, these hits greater than e-100 indicate a very good match.

EXAMPLE

The following example used a high-accuracy system of hidden Markov models (HMMs) for automated genome annotation. Proteins were annotated by competing batteries of HMMs to yield family designations. This HMM library was applied to exploring uncharacterized genes. The Generalized Rapid Automated Protein Analysis (GRAPA) system assesses annotation significance with a dynamic threshold, which compensates for the variance in the quality of distance calculations from one HMM to another. This example illustrates various aspects of the invention.

Figure 8:
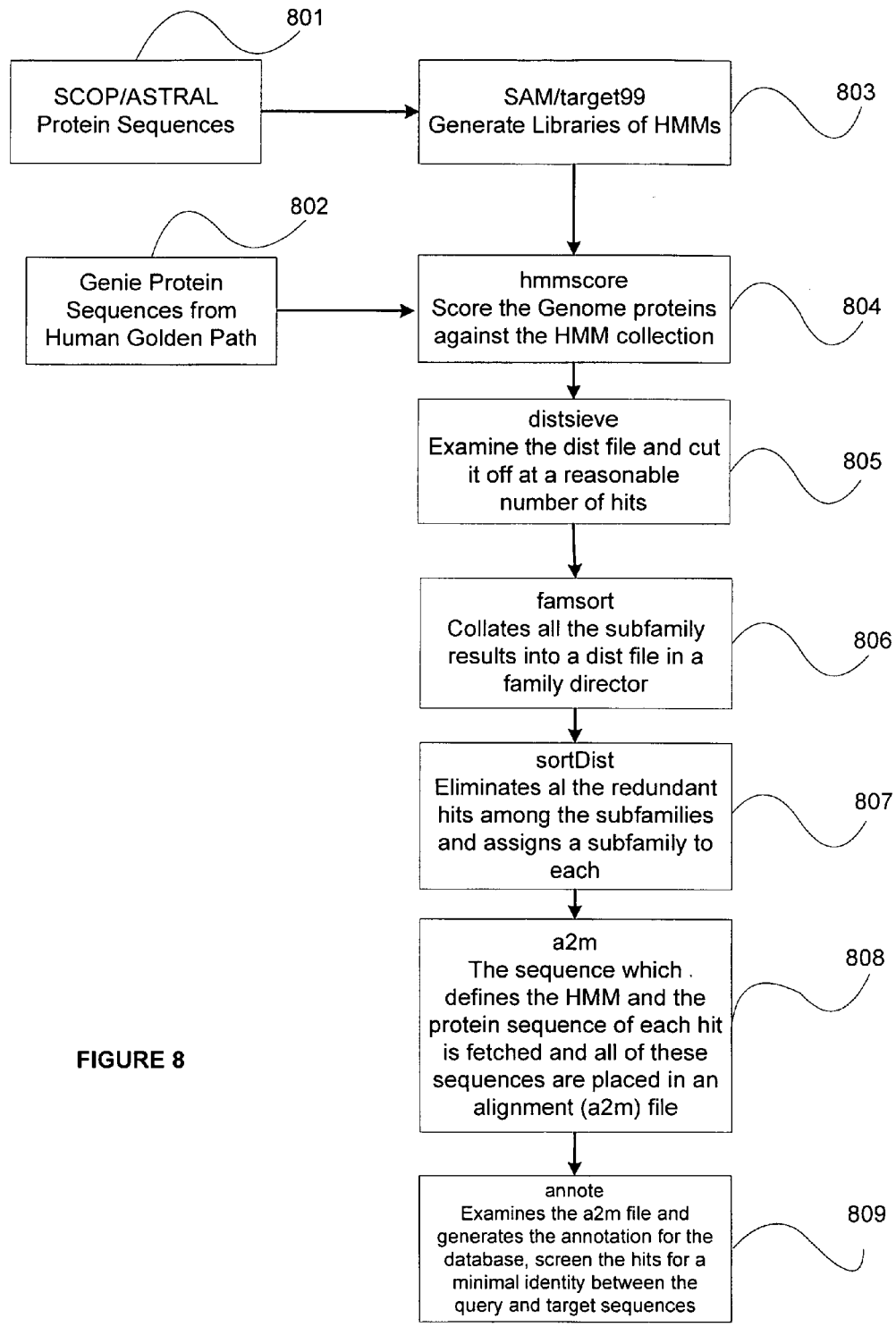
FIG. 8 is a schematic showing an exemplary embodiment of the process of the invention for characterizing genes.

A. Materials and Methods. FIG. 8 is a flow chart showing the steps of the method used in this example.

Whole genome gene set. A set of protein sequences covering the Golden Path of the human genome (Oct. 7, 2000 freeze World Wide Web Address: genome.ucsc.edu/) was generated by the Genie (Reese, M. G., Kuip, D., Tammana, H. and Haussler, D. (2000) Genie—gene finding in Drosophila melanogaster. Genome Res 10(4), 529–38) programs suite (Kulp, D. & Wheeler, R., available at the following URL (genome.ucsc.edu, last visited on Sep. 20, 2001), with the repeat regions masked out (802). The data set consists of three sets of amino acid sequences: (1) the set derived by alignment of mRNA to the genomic DNA corresponding to sequences in RefSeq and GenPept, (2) a set of alternatively spliced variants, which are generated using mRNA/EST-to-genomic alignments in combination with purely statistical methods, each of which contain the largest subset of exons for a particular gene, and (3) genes predicted by purely ab initio methods. These sequences are non-redundant; none of the included genes overlap the same genomic region. In cases where there were many genes overlapping the same region, the one with the longest CDS (translation) was kept. This set, known as annot10, contains 59,378 putative protein sequences.

Generating Hidden Markov Models. The GRAPA system characterizes each SCOP protein domain found in ASTRAL (Brenner, S. E., Koehl, P. and Levitt, M. (2000)(FIG. 8, 801). The ASTRAL compendium for protein structure and sequence analysis. Nucleic Acids Res 28(1), 254–6.) (v1.53), a web site which allows the user to set various parameters for selecting proteins from SCOP. For SCOP version 1.53, the total set of non-redundant proteins consisted of 4369 entries. Multiple species were included to capture entries with both mammalian and non-mammalian proteins.

For each entry in the SCOP protein set (FIG. 8, 803), a hidden Markov model (HMM) was built using the Sequence Alignment and Modeling system (SAM 3.0) target99 protocol (Karplus, K., Barrett, C. and Hughey, R. (1998). Hidden Markov models for detecting remote protein homologies. Bioinformatics 14(10), 846–56). It might seem redundant to build a model for each SCOP protein since there are sometimes proteins from multiple species, all of which are the same protein; however, it has been shown (Aravind, L. and Koonin, E. V. (1999). Gleaning non-trivial structural, functional and evolutionary information about proteins by iterative database searches. J Mol Biol 287(5), 1023–40) that models built with certain seed sequences will capture a broader set of hits. Therefore, one should know a priori which sequences to use or should exhaustively use them all. This protocol profiles the family of a seed sequence by iteratively searching for homologs of the seed sequence, estimating a multiple alignment of the seed sequence and its homologs, estimating an HMM from the multiple alignment, and using this HMM to search for additional homologs. At each iteration, the HMM yields a generalized profile of the sequence family, describing the salient characteristics expected in additional homologs not yet seen. The early iterations produce very specific profiles, recognizing only close homologs of the seed sequence. Each subsequent iteration yields a broader profile. The generality of each profile is controlled by the thresholds for admitting new sequences to the family. The E-value thresholds used for SAM-T99 are 0.001 and 0.02 for two cycles, higher than those suggested for superfamily HMM compilation (0.00001, 0.0001, 0.001, 0.01) and with fewer cycles (four is often used).

Screening Genes Against SCOP HMMs (804). After each gene had been scored against all the HMMs, it was assigned to one model according to the best score within the SCOP superfamily. Before accepting an annotation, the alignment to the model further evaluated by other metrics including sequence identity. In some cases, genes might fail to be annotated due to incorrect intron boundaries. However, those predicted genes that meet the thresholds for matching a particular family or superfamily, may be refined by mapping of known, related genes back onto the genomic DNA with programs like GeneWise (Birney, E. and Durbin, R. (2000). Using GeneWise in the Drosophila annotation experiment. Genome Res 10(4), 547–8). GRAPA then generated a report for a more careful examination of genes discovered de novo, integrating the protein annotation information into the gene-finding process.

Assigning Annotations Based on SCOP Family with Distsieve (805). A correspondence between a SCOP family and a gene was based on the E-value scored by SAM-T99. The program distsieve (attached computer program listing) examined all the sequences scored against a particular SCOP model. Because the interpretation of distance scores, expressed as logarithmic E-values was dependent upon the HMM generated for each sequence, there is no single E-value threshold that can be applied to all models. Instead, for each HMM, the distsieve method examined the set of scores by curve analysis to determine a reasonable E-value threshold. The distance scores included controls representing the proteins used to build all the models; thus, the best hit was often the seed sequence for the HMM.

Five criteria were used to distinguish the hits to be kept: (1) when the E-values rose above a value of e-05 they were discarded regardless of the other criteria; (2) the first ten hits were kept provided they score better than e-05; (3) the hits more than 70% of the log of the maximum score were automatically kept; (4) the point where the E-value plot drops abruptly or flattens was used as a threshold; (5) no more than a maximum number of hits (e.g., 1000) are kept.

Next, the set of hits accepted by distsieve were grouped by superfamily (806), where each gene is assigned to one SCOP family HMM according to the best distance score. While SAM-T99 was designed and optimized for superfamily recognition, GRAPA was designed for function prediction at the family level. Among the representative HMMs in the superfamily, the scores for each hit was compared and assigned to the family which generated the best score by the program, sortDist (807). The program, align2model was used to create an alignment between a successful hit and the SCOP sequence according to the SAM-T99 generated model (808). The alignments were then screened by identity scores and annotations created in XML database format (809).

RESULTS AND DESCUSSION. Model Validation. All SCOP sequences were scored against each model to assess the accuracy of the model library. The hits to each model were assessed before and after the distsieve threshold. Each SCOP control sequence hit was classified as a family hit (true positive) or false positive according to its relation to the model's seed sequence; true positives are defined as members of the same SCOP family, while false positives were members of different SCOP families.

For each model, sensitivity, the percentage of correct SCOP family members found; selectivity, the percentage of SCOP family members found among the hits were evaluated. Thus, GRAPA was designed to be very selective, even at the expense of some potential sensitivity.

most of the family-level homologs. After applying distsieve, the performance of GRAPA was comparable to that of PSI-BLAST, with PSI-BLAST getting slightly more hits and a slightly lower selectivity.

TABLE 2

Model sensitivity. On average, each SCOP HMM finds 93.6% of its actual family members before the distsieve threshold, and 77.2% after the distsieve threshold. While distsieve cuts out some number of family hits, false positives present a bigger problem in gene annotation than false negatives. PSI-BLAST sensitivity figures are shown for comparison.

|  | Mean | Total |
|---|---|---|
| SCOP family members | 22 | 97,282 (100%) |
| SCOP family hits before distsieve threshold | 21 | 91,024 (93.6%) |
| SCOP family hits after distsieve threshold | 17 | 75,036 (77.2%) |
| PSI-BLAST hits | 17 | 77,950 (80.1%) |

Table 2 shows the sensitivity of the annotation process in comparison to PSI-BLAST. For each model, the number of SCOP family hits was compared to SCOP family members. Each sequence had an average of 22 SCOP family members. 21 of these were among the top hits to the model, and 17 were selected by distsieve. Thus, while some family members were lost in the selection process, most (77.2%) were not.

The distsieve threshold was weighted against a simple BLAST E-value threshold. This number of false positives would be accepted if an E-value threshold of 1.0e-86 was applied to all models. Note that this E-value threshold would admit only 21,799 family members. By using the distsieve threshold for each model rather than an E-value threshold,

TABLE 1

Model selectivity. True positives are defined as control sequences from the same SCOP family as the seed sequence, and false positives are defined as SCOP sequences from different SCOP families than the seed sequence. PSI-BLAST selectivity figures are shown for comparison.

| Control (SCOP) hits, all models | Before distsieve threshold mean | total | After distsieve threshold mean | total | PSI-BLAST Mean | total |
|---|---|---|---|---|---|---|
| Total control (SCOP) hits | 114 | 497,509 | 18 | 79,578 | 18 | 82876 |
| Family members (true positives) | 21 | 91,024 (18.3%) | 17 | 75,036 (94.3%) | 17 | 77,950 (94.1%) |
| False Positives | 93 | 406,485 (81.7%) | 1 | 4,542 (5.7%) | 1 | 4,926 (5.9%) |

Table 1 describes the selectivity of the annotation process in comparison to the standard method PSI-BLAST (Altschul, S. F., Madden, T. L., Schaffer, A. A., Zhang, J., Zhang, Z., Miller, W. and Lipman, D. J. (1997). Gapped BLAST and PSI-BLAST: a new generation of protein database search programs. Nucleic Acids Res 25(17), 3389–402). Before applying distsieve, the hits to each model included an average of 114 SCOP sequences: 21 family hits and 93 false positives. After applying distsieve, the hits to each model included 18 control sequences: 17 family hits and 1 false positive. The percentage of false positives at the family level was 81.7% before any threshold is applied. After distsieve, this value dropped to 5.6%. Thus, distsieve succeeded in weeding out most of the false positives while preserving three times as many family members (75,036) were admitted for a comparable number of false positives. The lowest E-value threshold that would admit 75,036 family members is 1.0e-22; at that threshold, 32,822 false positives would be admitted.

As shown in Tables 1 and 2, the selectivity of PSI-BLAST and GRAPA are comparable. Further, in detailed examination of the results, GRAPA and PSI-BLAST tend to score well in the same cases, and score poorly in the same cases. In general, both methods perform worst in cases such as globins and EF-hands, when some SCOP superfamily contains a number of closely-related families. In such cases, this behavior should be viewed as an effect of where the threshold was drawn in the SCOP hierarchy.

Protein Phosphatase Candidates in the Human Genome. To compare GRAPA to other high-throughput homology search methods, searches were performed on protein phosphatases, enzymes that remove phosphate groups from proteins at specific amino acid side chains. The amino acid sequences for the SCOP phosphatase domains (Table 3) were run through BLASTP and PSI-BLAST (with a threshold of 1e-05) and compared to the results from GRAPA with distsieve threshold. The resulting hits were compared using identity scores by pairwise CLUSTALW alignments between each hit and the five target sequences, where the best identity score kept for each hit.

TABLE 3

Full genome protein set scored against SCOP hidden Markov models. Known Genie-derived phosphatases from GenBank are separated out, showing that they are all identified by three models: 2567, 3788, and 3795.

| HMM ID | PDB code | SCOP ID | protein name | Number GenBank Entries | Number non-GenBank Entries |
|---|---|---|---|---|---|
| 692 | 1a17 | 1.111.8.1.1 | Protein phosphatases 5 (Human) | 1 | 78 |
| 694 | 1qqe | 1.111.8.1.3 | Vesicular transport protein sec17 (yeast) | — | 4 |
| 2567 | 1vhr | 3.40.1.1.1 | VH1-related dual-specificity phosphatases, VHR (Human) | 6 | 52 |
| 3788 | 1a6q | 4.144.1.1.1 | protein Ser/Thr phosphatases 2C (Human) | 3 | 2 |
| 3793 | 1fjm | 4.145.1.3.1 | protein phosphatases-1 (PP-1) (rabbit) | 5 | 7 |
| 3794 | 1tco | 4.145.1.3.2 | protein phosphatases-2B calcineurin A submit (bovine) | 2 | — |
| 3795 | 1aui | 4.145.1.3.3 | protein phosphatases-2B calcineurin A submit (Human) | 1 | — |
| Total | | | | 18 | 143 |

Of the 18 Genie-derived human protein phosphatases in GenBank, every one mapped to the SCOP phosphatase families with better than 20% sequence identity, as shown in Table 3. As in Table 4, GRAPA found the most phosphatase candidates, PSIBLAST, nearly as many, and BLASTP only one third as many.

TABLE 4

Identity of GRAPA verses BLAST candidates for GenBank and novel hits divided by whole sequence percent identity against the SCOP seed sequences for relevant families (Table 3). Novel hits, in parentheses, are those found exclusively by these methods.

| Percent Identity | GRAPA (HMM) | PSIBLST | BLASTP | GENBANK |
|---|---|---|---|---|
| 0–5% | 0 | 0 | 0 | 0 |
| 5–10% | 0 | 1 (1) | 0 | 0 |
| 10–15% | 10 (5) | 6 (1) | 2 | 0 |
| 15–20% | 15 (6) | 12 (3) | 1 | 0 |
| 20–25% | 69 (27) | 47 (5) | 13 | 0 |
| 25–30% | 30 (7) | 24 (0) | 14 | 3 |
| 30–40% | 16 | 16 | 16 | 5 |
| 40–50% | 4 | 4 | 4 | 4 |
| 50–50% | 0 | 0 | 0 | 0 |
| 60–70% | 0 | 0 | 0 | 0 |
| 70–80% | 1 | 1 | 1 | 0 |
| 80–90% | 2 | 2 | 2 | 2 |
| 90–100% | 4 | 4 | 4 | 4 |
| Total | 151 | 117 | 57 | 18 |
| Known (GenBank) | 18 | 18 | 18 | 18 |
| Novel | 45 | 10 | 0 | — |

BLASTP is the most conservative of the three methods with only 57 total hits. These hits include the 18 known protein phosphatases in human annot10 gene set; all exhibit greater 30% sequence identity to a seed sequence.

From table 4, it is clear that the methods vary mostly in sensitivity. GRAPA finds 30% more candidates than PSI-BLAST. PSI-BLAST finds 11 candidates which the other methods do not find and GRAPA finds 45 hits unique to it, whereas BLASTP found essentially no unique hits. In the grey, 20–30% identity range, for homologues, PSI-BLAST and family HMMs performance are known to be comparable, but GRAPA found more candidates with identity scores in every identity bracket, finding seven unique candidates with 25–30% identity while PSI-BLAST found only one.

FIG. 9 shows phosphatase alignments. Alignment 1: A protein found similar to VHR dual specificity phosphatase (1 vhr), with a probable insert domain. The catalytic cysteine as position 301 is conserved. Alignment 2: Proteins found with the fold of protein phosphatase 5 (1a17).

Figure 10:
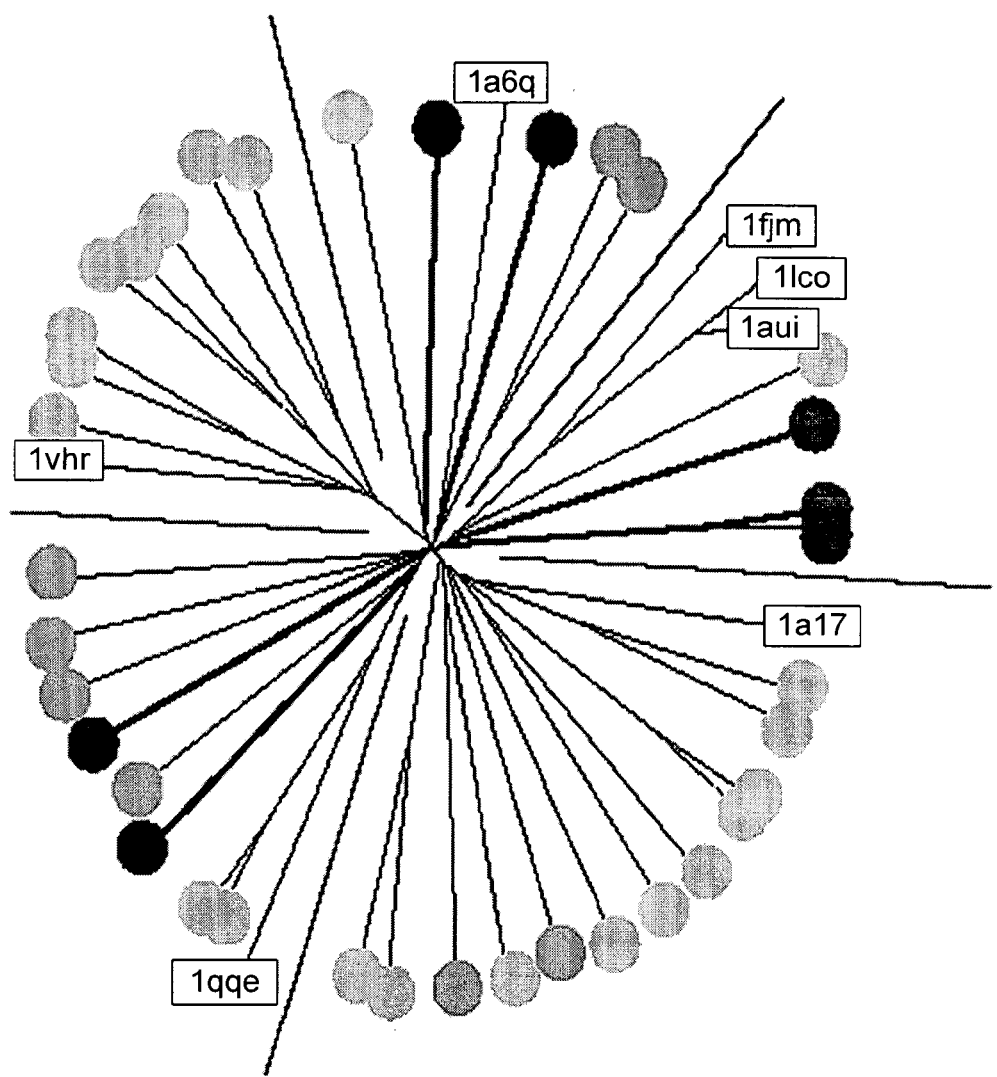
FIG. 10 shows a dendrogram of top phosphatase hits (greater than or equal to 25% sequence identity to seed sequences).

FIG. 10 shows a dendrogram of top phosphatase hits (greater than or equal to 25% sequence identity to seed sequences). Triangle nodes are seed sequences from SCOP representing separate families; each triangle node corresponds to an HMM. The 1 fjm, 1 tco, and 1 aui nodes are members of the same SCOP family. Light filled nodes are hits found by all three methods including BLASTP. Intermediate filled nodes represent sequences found by both GRAPA and PSI-BLAST. The dark nodes are the novel hits found by GRAPA. There are no novel nodes found by PSI-BLAST which have greater than 25% identity to a seed sequence.

Genome analysis by GRAPA. An overview of human genes shows a concordance between GRAPA and PFAM. The most common SCOP domains in the human annot10 gene set are shown in Table 5. The corresponding Pfam domain and rank in the human genome is provided for each of the top twenty SCOP domains. In general, these numbers are equivalent to those previously published for the Fly genome by the application of the InterPro analysis (Rubin, Yandell et al. 2000). PFAM confirms the top ten GRAPA domains; kinases, zinc fingers, G proteins, ankyrin repeats, SH3-domain family and WD repeats.

TABLE 5

Most frequently occurring domains of human genes according to GRAPA (SCOP v 1.53) and PFAM. Rank in Pfam column is from the equivalent Pfam family ranking (not shown)

| | SCOP Family Id | H | SCOP family | Pfam (rank equivalent) |
|---|---|---|---|---|
| 1 | 4.130.1.1 | 349 | Serine/threonine kinases | pkinase (3) |
| 2 | 7.37.1.1 | 296 | Classic zinc finger, C2H2 | zf-C2H2 (1) |
| 3 | 4.130.1.2 | 246 | Tyrosine kinase | pkinase (3) |
| 4 | 3.32.1.8 | 184 | G proteins | ras (20) |
| 5 | 1.111.2.1 | 135 | Ankyrin repeat (SH3-domain superfamily) | ank (5) |
| 6 | 2.64.3.1 | 115 | Trp-Asp repeat (WD-repeat) | WD40 (8) |
| 7 | 3.9.2.1 | 99 | Internalin B LRR domain | LRR (9) |
| 8 | 3.9.2.3 | 97 | U2A'-like Leucine Rich Repeat Fold, RNA recog. | LRR (9) |
| 9 | 3.32.1.13 | 90 | Extended AAA-ATPase domain (DNA helicases bacterial yeast) | helicase_C (26) and DEAD (27) |
| 10 | 3.9.1.2 | 86 | Rna1p (in Leucine Rich Fold) | LRR (9) |
| 11 | 2.44.1.2 | 82 | Eukaryotic proteases | — |
| 12 | 2.44.1.1 | 78 | Prokaryotic proteases | — |
| 13 | 1.4.1.1 | 74 | Homeodomain | homeobox (14) |
| 14 | 4.37.1.1 | 73 | BTB/POZ domain (zinc finger) | BTB (24) |
| 15 | 1.23.1.1 | 65 | Nucleosome core histones | histone (29) |
| 16 | 3.9.1.1 | 64 | Ribonuclease inhibitor (LRR fold) | LRR (9) |
| 17 | 4.82.1.1 | 63 | SH2 domain | SH2 (25) |
| 18 | 3.9.2.2 | 63 | Rab geranylgeranyl-transferase a-subunit, N-terminal (C2 domain-like Fold) | C2 (22) |
| 19 | 2.1.1.1 | 61 | V set domains (Ab variable domain-like) Ig superfamily | Ig (4) |
| 20 | 3.32.1.9 | 61 | Motor proteins (nucleoside triphosphate hydrolase fam) | myosin head motor domain (52) |

While SCOP defines (and GRAPA identifies) leucine rich repeats (LRRs) via their presence as part of whole proteins, Pfam has a specific domain (LRR) which identifies this motif independent of the protein type. This difference gives rise to the disparities of the figures in SCOP where LRRs appear as Internalin B LRR domain, U2A'-like (Leucine Rich Repeat Fold and RNA recognition), and Rna 1 p (in Leucine Rich Fold).

Significant differences between GRAPA and PFAM are attributable to differences in the construction between the two suites. SCOP groups eukaryotic and prokaryotic proteases under the trypsin-like serine protease superfamily. The eukaryotic family contains 39 different proteases and the prokaryotic family contains nine different proteases. The trypsin Pfam domain appears to be more specific and would likely not rank in the top twenty. Immunoglobulin domains appear as a top hit under Pfam (rank=4), while SCOP finds many such hits via the V set domains (antibody variable domain-like) (rank=19).

Given the high rank of the Zinc finger C3HC4 type RING domain (rank=13) in the Pfam top twenty, and the RING models in SCOP (rank=90), more careful examination would be required to determine whether these Pfam hits appeared in the SCOP C2H2 (rank=2) or BTB/POZ zinc finger (rank=14) domains. In the case for the Pfam EF-HAND domain (rank=15), SCOP has broken the EF-hand superfamily into seven families, which would yield fewer hits per family and therefore make them less likely to appear in the top twenty models.

The prevalence of signaling proteins such as kinases, proteases, and G proteins in the human genome reflects the importance and variety of signaling mechanisms within higher-order organisms such as humans.

The top twenty Pfam entries (data not shown) with no corresponding SCOP entry, correspond to transmembrane proteins (7tm_1) and other entries for which there are no solved 3D structures.

The annotation and examination of genome-derived sequences for known classes of proteins is an important approach for exploring the new biological data in silico. More than 40% of the current genes in the genome are previously uncharacterized and the combination of protein categorization schemes with the unknown genes will be very useful for that work. The GRAPA method successfully assigns genes to SCOP families based on a highly automated and accurate scoring method against a battery of hidden Markov Models. Its performance is comparable to PSI-BLAST. The entire human genome (known and predicted) has been screened against these models. Results similar to PFAM were found, where the top categories of genes overlapped considerably.

In a general comparison, GRAPA's performance was found to be similar to that of PSI-BLAST. In a more detailed comparison, searching on phosphatases, GRAPA found 20% more candidates of comparable quality than PSI-BLAST, and nearly three times as many hits as BLASTP.

With the innovation of using curve analysis to analyze high throughput HMM scores, independent of the HMMs' properties, GRAPA could be configured, without extensive manual intervention, to reflect varied ontological or biochemical categorization schemes for which protein sequences are available. With a scheme such as GRAPA, HMMs may be generated from a plethora of diverse protein databases, allowing the identification of the potential function on the sets of new genes being identified in the genome.

The GRAPA methodology was also applied to the Enzyme Commission classification scheme. This scheme contains a hierarchical representation based on broad enzymatic classes, sets of substrates, and cofactors/reagents. Enzymes are principally classified and named according to the reaction they catalyze. The highest level distinction, the enzyme class is broken into oxidoreductases, transferases, hydrolases, lyases, isomerases, and ligases. The next level of distinction in the EC hierarchy is the substrate upon which the enzyme acts, for example, CH—OH, aldehyde, CH—NH2, etc. The third level is the co-factor or reagent required for conversion of the substrate. These reagents might include NAD+, NADP+, oxygen, quinone, etc.

For each enzyme in the EC set, an HMM was built using SAM-T99. Model building and scoring were performed in a similar manner to SCOP. Since EC is a hierarchical classification scheme with a tree structure, a set of hits to HMMs may be grouped into superfamilies. Putative hits were assigned to a single EC HMM within each superfamily according to the best E-value, and this HMM was used to align the query sequence to the EC sequence.

In instances, the annotations were stored in a Relational Database Management system, i.e., postgres. This affords the following advantages: a)—data format is secured from errors by the data types of the table schemas; b)—the pipeline can be recovered if it is interrupted.

In some instances, the alignments of the sequences are checked for quality and removed before they are accepted by the famsort algorithm (which is now a series of database commands), e.g, the number of gaps in the alignment of the hit and the size of the largest gap are set at 8 and 40 respectively.

It is to be understood that the above description is intended to be illustrative and not restrictive. Many embodiments will be apparent to those skilled in the art upon reviewing the above description. The scope of the invention should, therefore, be determined not with reference to the above description, but should instead be determined with reference to the appended claims, along with the full scope of equivalents to which such claims are entitled.

PROGRAM LISTING DEPOSIT

```perl
Copyright 2001, Affymetrix, Inc.
#!/usr/bin/perl -w
# distsieve - a perl script to collate and sort hmmscore output
# use: distsieve [FAMILYNAME]
use strict;
# parameters for the filter
my $maxE      = -8;       # highest allowed E value (log 10)
my $maxN      = 1000;     # maximum number of hits per dist file
my $DEFminN   = 10;       # number of hits before looking for a cut
my $Efrac     = 0.8;      # log fraction of Emax where we start loo
my $minE      = -50;      # default minE -calculated in pass1
# other variables
my @files;
my $family    = "sieve";
my $minN      = $DEFminN;
my $logmax;
my @delta;
my @eval;
my @elog;
my @entries;
my @drop;
my $ndrop;
my $emin      = 2.0e00;
my $emax      = -1.0e00;
my $cutoff    = $maxN;
my $fnum      = 0;
my $ecount    = 0;         # entries read in
my $totcnt    = 0;
my $tottot    = 0;
# decide mode
if ($ARGV[0]) {
    $family = $ARGV[0];
# modified for SCOP
    @files = <GLOB*/*/*.dist>;
} else {
    @files = <*dist>;
}
# initialize - open files
open DISTOUT,">$family.ds.dist" || die "can't open DISTOUT\n";
open LOG, ">$family.distsieve.log";
#open FAMOUT, ">$family.list" || die "Can't open $family.list\n";
print LOG "\#DistSieve Log - totals are hits below $maxE - ";
print LOG scalar localtime;
print LOG "\nFile Name\t\t\tN. hits \tEmin \t\tEmax \t\tplotfile\n";
foreach my $file (@files) {
    $fnum++;
    $minN = $DEFminN;
#   print FAMOUT ">$fnum $file\n";
    open INFILE, "<$file" || die "can't open $file\n";
    my $comment = "";
###############################################
# read in each file gather statistics
# cutoff only if > maxN hits are obtained
# or if there are less than $DEFminN hits
###############################################
    my @entries;
    $ecount = 0;
    while (<INFILE>) {
        if (/%/) {
            $comment .= $_;
        } else {
# get some max val stats and cutoff at $maxE
            chomp;
            $entries[$ecount] = $_;
# get emin cutoff emax
            my @toks = split /\s+/, $entries[$ecount];
            $eval[$ecount] = $toks[4];
            @toks = split /e/, $eval[$ecount];
            $elog[$ecount] = $toks[1];
            $delta[$ecount] = $elog[$ecount] - $elog[$ecount-1];
```

-continued

```
            if ($ecount == 0) {
                $emin = $eval[0];
                $logmax = $elog[0];
                $minE = $logmax * $Efrac;
            }
if ( ($ecount < $DEFminN) && ($elog[$ecount] > $maxE) && $minN==$DEFmi
            $minN = $ecount;
            goto PASS2;
    }
    if ($ecount > $maxN) {
            goto PASS2;
    }
        $ecount++;
        }
} # while
#############################################
# perform analysis, get cutoff
#############################################
PASS2:
    $cutoff = 0;
    $ndrop = 0;
    for (my $i=$minN; $i < $ecount; $i++) {
# enforce E value cutoffs
        if ($elog[$i] < $minE) {
            next;
        }
        if ( $elog[$i] > $maxE ) {
            if ($cutoff < 1) {
            $cutoff = $i;
            }
        }
    # do curve analysis here
        if ( ( ($delta[$i] > $delta[$i -1]) && ($delta[$i] < 5) && ($delt
            if ($cutoff < 1) {
                $cutoff = $i;
            }
            $drop[$ndrop] = $i;
            $ndrop++;
        }
    }
    if ($cutoff==0) { $cutoff = $minN }
PLOT:
    $emax = $eval[$cutoff];
    print "$file has $cutoff / $ecount entries emin:$emin emax:$emax logm
#############################################
# output the saved up file, a plot of cutoff
#############################################
open PLOTTEMP, ">temp.dat" || die "can't open plot data file\n";
    for (my $i=0; $i < $ecount; $i++) {
        print PLOTTEMP "$elog[$i]      $minE    $maxE\n";
    }
close PLOTTEMP;
# output DIST
$totcnt += $cutoff;
$tottot += $ecount;
my $ylab = $elog[$cutoff] -3;
print DISTOUT "==> $file <==\n";
print DISTOUT "$comment";
print LOG "$file        $cutoff/$ecount     \t$emin   \t$emax   $minE $ndrop\t\t
open TEMP, ">plot.temp";
my $tmp = $file;
$tmp =~ s/\_/ /g;
print TEMP "set title \"HMM SCREENS FROM $tmp\"\n";
print TEMP "set out \"$file.ps\"\n";
print TEMP "set ylabel \"E value\"\n";
print TEMP "set xlabel \"Hit #\"\n";
print TEMP "set size 1.0, 0.5\n";
print TEMP "set terminal postscript portrait enhanced \"Helvetica\" 14\n";
print TEMP "set label \" | cutoff\" at $cutoff, $ylab \n";
print TEMP "plot \"temp.dat\" using :1 title \"E scores\" with lines, \\\
print TEMP " \"temp.dat\" using :2 title \"E_M_i_n\" with lines, \\\n";
print TEMP " \"temp.dat\" using :3 title \"E_M_a_x\" with lines\n";
close TEMP;
    for (my $i=0; $i < $cutoff; $i++) {
        print DISTOUT "$entries[$i]\n";
    }
# gnuplot our file
close TEMP;
`gnuplot plot.temp`;
```

-continued

```
'rm -f plot.temp';
'rm -f temp.dat';
}        #foreach
print LOG "--------------------------------------------------------
TOTAL    \t\t\t$totcnt/$tottot hits in $fnum files \n";
close LOG;
close DISTOUT;
#close FAMOUT;
exit;
```

The invention claimed is:

1. A computer implemented method for gene characterization comprising:
   generating a plurality of models using structural relationships of known proteins;
   inputting a plurality of protein sequences;
   determining a plurality of scores by comparing the plurality of protein sequences with the plurality of models;
   automatically selecting a plurality of hits based on at least the plurality of scores; and
   assigning the plurality of protein sequences to the plurality of models based on at least the plurality of selected hits;
   wherein:
   the automatically selecting a plurality of hits comprises determining a threshold for each of the plurality of models;
   the determining a threshold comprises performing a curve analysis.

2. The method of claim 1 wherein the plurality of models comprises hidden markov models.

3. The method of claim 1 wherein the plurality of protein sequences comprises 50 protein sequences.

4. The method of claim 3 wherein the plurality of protein sequences comprises 150 protein sequences.

5. The method of claim 4 wherein the plurality of protein sequences comprises 500 protein sequences.

6. The method of claim 1 wherein the performing a curve analysis comprises analyzing a plurality of slopes for a plurality of curves.

7. A system for gene characterization comprising a processor; and a memory coupled with the processor, the memory storing a plurality of machine instructions that cause the processor to perform logical processes comprising:
   generating a plurality of models using structural relationships of known proteins;
   inputting a plurality of protein sequences;
   determining a plurality of scores by comparing the plurality of protein sequences with the plurality of models;
   automatically selecting a plurality of hits based on at least the plurality of scores; and
   assigning the plurality of protein sequences to the plurality of models based on at least the plurality of selected hits;
   wherein:
   the automatically selecting a plurality of hits comprises determining a threshold for each of the plurality of models;
   the determining a threshold comprises performing a curve analysis.

8. The system of claim 7 wherein the plurality of models comprises hidden markov models.

9. The system of claim 7 wherein the plurality of protein sequences comprises 50 protein sequences.

10. The system of claim 9 wherein the plurality of protein sequences comprises 150 protein sequences.

11. The system of claim 10 wherein the plurality of protein sequences comprises 500 protein sequences.

12. The system of claim 7 wherein the performing a curve analysis comprises analyzing a plurality of slopes for a plurality of curves.

13. A computer software product for gene characterization comprising a computer readable medium having computer executable instructions for performing the method comprising:
   generating a plurality of models using structural relationships of known proteins;
   inputting a plurality of protein sequences;
   determining a plurality of scores by comparing the plurality of protein sequences with the plurality of models;
   automatically selecting a plurality of bits based on at least the plurality of scores; and
   assigning the plurality of protein sequences to the plurality of models based on at least the plurality of selected hits;
   wherein:
   the automatically selecting a plurality of hits comprises determining a threshold for each of the plurality of models;
   the determining a threshold comprises performing a curve analysis.

14. The product of claim 13 wherein the plurality of models comprises hidden markov models.

15. The product of claim 13 wherein the plurality of protein sequences comprises 50 protein sequences.

16. The product of claim 15 wherein the plurality of protein sequences comprises 150 protein sequences.

17. The product of claim 16 wherein the plurality of protein sequences comprises 500 protein sequences.

18. The product of claim 13 wherein the performing a curve analysis comprises analyzing a plurality of slopes for a plurality of curves.

* * * * *